United States Patent [19]

Hoppe et al.

[11] Patent Number: 4,617,390

[45] Date of Patent: Oct. 14, 1986

[54] S-TRIAZINE DERIVATIVES

[75] Inventors: Udo Hoppe, Hamburg; Karl Seib, Weinheim; Paul Naegele, Neuhofen; Roland Martin, Kaiserslautern, all of Fed. Rep. of Germany

[73] Assignee: BASF Aktiengesellschaft, Rheinland-Pfalz, Fed. Rep. of Germany

[21] Appl. No.: 741,194

[22] Filed: Jun. 4, 1985

Related U.S. Application Data

[63] Continuation of Ser. No. 467,745, Feb. 18, 1983, abandoned.

[30] Foreign Application Priority Data

Feb. 23, 1982 [DE] Fed. Rep. of Germany ....... 3206398

[51] Int. Cl.$^4$ .......................................... C07D 251/70
[52] U.S. Cl. .................................................... 544/197
[58] Field of Search .................... 544/197; 424/59, 60

[56] References Cited

U.S. PATENT DOCUMENTS

| | | | |
|---|---|---|---|
| 3,249,608 | 5/1966 | Biland et al. | 260/248 |
| 3,278,253 | 10/1966 | Weckler et al. | 544/197 |
| 3,400,121 | 9/1968 | Weckler et al. | 544/197 |
| 3,697,520 | 10/1972 | Winter | 260/249.6 |
| 4,096,206 | 6/1978 | Boyer | |
| 4,183,929 | 1/1980 | Conrow | 544/197 |
| 4,402,907 | 9/1983 | Clark | 422/7 |
| 4,438,094 | 3/1984 | Oppenlaender et al. | 424/59 |

OTHER PUBLICATIONS

*Chem. Abstr.*, vol. 87, 1977, No. 87:85298x, Alksnis et al., "Synthesis of oligoesters and polyesters from oxalic acid and ethylene glycol", p. 3.

*Chemische Rundschau*, No. 34, Oct. 27, 1971, Roland Voegeli, "Ueber die Auswahl von modernen Sonnenschutzmitteln", pp. 1097–1098.

*Primary Examiner*—John M. Ford
*Attorney, Agent, or Firm*—Oblon, Fisher, Spivak, McClelland & Maier

[57] ABSTRACT

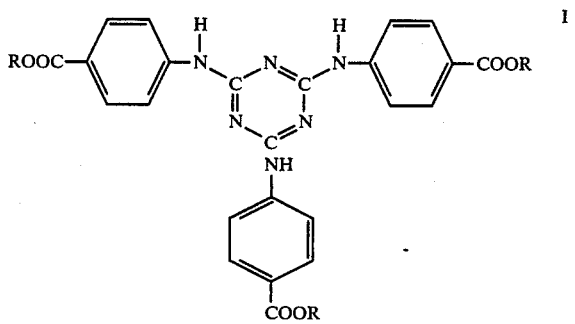

where the individual radicals R are identical or different and are each hydrogen, an alkali metal, or ammonium which is unsubstituted or substituted by organic radicals, or are each $C_1$–$C_{20}$-alkyl or a polyoxyethylene radical which contains from 1 to 10 ethylene oxide units and whose terminal OH group may be etherified by an alcohol of 1 to 3 carbon atoms, are used as sun screen agents.

3 Claims, No Drawings

S-TRIAZINE DERIVATIVES

This application is a continuation of application Ser. No. 467,745, filed Feb. 18, 1983, now abandoned.

The present invention relates to the use of certain s-triazines, which are substituted at the carbon atoms by radicals of p-aminobenzoic acid, its salts and/or its alkyl or polyethylene glycol esters, as sun screen agents for the human skin and also as light stabilizers in the industrial sector.

The present invention furthermore relates to novel s-triazines which are substituted at one or more carbon atoms by radicals of a p-aminobenzoic acid ester and at the remaining carbon atoms by the above radicals.

It is known that the region of from 280 to 320 nm of sunlight or artificial light sources is responsible for the development of erythema on human skin, this light region being referred to as ultraviolet-B radiation. The maximum activity of ultraviolet radiation in respect to erythema formation is at 297 nm if the radiation intensity is equally great for all wavelengths. In sunlight, containing radiation of varying intensity, the maximum effect is shifted to 308 nm.

By using suitable filter substances for the ultraviolet-B range, erythema formation can be at least retarded. On the other hand, it is desired that pigment formation in the skin, which is the cause of bronzing, should not be suppressed.

Ultraviolet radiation is furthermore an important factor in the aging of polymers and can also, for example, effect a change in certain dyes or decomposition of the polymer molecule itself, so that for these products, again, filter substances which act as stabilizers are virtually indispensable.

In the past 40 to 50 years, a large number of compounds have been examined for filter action in the ultraviolet-B range. In these investigations, which were concerned particularly with compounds for protecting the human skin from the sun, it was necessary to take into account the filtering efficiency in the erythema-forming range as well as to ensure that permeability in the range of ultraviolet-A radiation was maintained, this radiation being responsible for pigment formation. Finally, such substances should also be tolerated by skin and mucous membrane and be non-toxic, and should not be decomposable by oxygen, heat and ultraviolet radiation. Important requirements of the cosmetics industry also include long shelf life, lack of intrinsic smell, and compatibility with the other cosmetic raw materials conventionally used.

In practice, from among the large number of compounds tested only a relatively small number of classes of substance have proved suitable in respect of the above requirements (in this context, reference may be made to Chemische Rundschau 24 (1971), 1097 et seq. This reference mentions, for example, p-methoxycinnamates, p-aminobenzoates and hydroxybenzophenone as such classes of substance.

A disadvantage of these compounds and of many compounds not mentioned in this reference is that they have to be used in an amount which is too high for optimum efficiency; it is desirable to avoid as far as possible such large amounts in cosmetic formulations since otherwise adverse side-effects may occur even in the case of substances whose toxicities have been determined to be very low.

It is an object of the present invention to provide substances which, when used in a very low dose, display a very powerful protective action against light as well as possessing good permeability to pigment-forming ultraviolet-A radiation, and otherwise fulfill all criteria in respect of stability, non-toxicity, and compatibility with the other cosmetic auxiliaries, and, where they are nonsoluble, also in respect of their emulsifiability or dispersibility in the cosmetic carriers.

We have found, surprisingly, that this object is achieved by compounds as defined in the claims.

Particularly good results are obtained with the novel compounds as defined in claims 2 and 3.

These compounds are reaction products of cyanuric chloride or bromide (2,4,6-trichloro-s-triazine or 2,4,6-tribromo-s-triazine) with p-aminobenzoates which may be completely or partially hydrolyzed to the free acids or their salts, or completely or partially transesterified with polyethylene glycols.

The free acids are disclosed in Chem. Abst. Vol. 87 (1977), 85,289 v; according to this reference, they are used as intermediates for further syntheses, but not as sun screen agents or cosmetic auxiliaries. The esters, however, are not described in the literature.

The s-triazine derivatives used in accordance with the invention can be prepared from cyanuric chloride or cyanuric bromide, preferably the former, and a $C_1$–$C_{20}$-alkyl ester or a polyoxyethylene ester of p-aminobenzoic acid; the polyoxyethylene ester contains from 1 to 10 ethylene oxide units and its terminal OH group can be etherified by an alcohol of 1 to 3 carbon atoms. From 3 to 4 moles of the ester are employed per mole of cyanuric chloride or bromide.

The resulting esters of the formula I, in particular the lower alkyl esters, may, if desired, then be converted to the free acids or their salts, this being done by hydrolysis. To obtain a novel compound as defined in claim 2 or 3, the ester is reacted with not more than two thirds of the amount of hydrolyzing agent necessary for the hydrolysis. Examples of hydrolyzing agents are NaOH, KOH, $Na_2CO_3$, $K_2CO_3$, $NH_3$, mono-, di- and tri-$C_1$–$C_4$-alkylamines and mono-, di- and tri-$C_2$–$C_4$-alkanolamines. This procedure gives the salts, which can be converted to the free acids by acidification. It is also possible to convert the ester directly to the acid using, for example, sulfuric acid or hydrochloric acid, but this method frequently leads to cleavage (hydrolysis) of the molecule.

The free acid containing three carboxyl groups in the molecule can also be obtained by directly reacting cyanuric chloride or bromide with p-aminobenzoic acid; however, this reaction is disclosed in the above Chem. Abst. reference.

The free acid containing three carboxyl groups can also be directly esterified, particularly in the case of polyoxyethylene radicals.

Furthermore, the esters with lower alkyl radicals can be transesterified with other alcohols by a conventional method.

For the purposes of the invention, preferred compounds are the esters conforming to the above definition, the 2-ethylhexyl ester and the 3,5,5-trimethylpentyl ester (isononyl ester) being particularly preferred among these. Polyethylene glycols containing from 2 to 6 ethylene oxide units and the methyldiglycol ester are preferred. The lower esters, in particular the methyl ester, are mainly used as intermediates for the preparation of the free acids, salts or polyethylene glycol esters.

The compounds according to the invention absorb, with very high extinction, in the ultraviolet-B range. By varying the radicals R, compounds having a particular consistency and the desired properties in respect of solubility and emulsifiability can be prepared. The compounds used according to the invention are chemically easily accessible and constitute an advantageous enrichment of the range of available sun screen agents. Thus, a range of compounds from those which are soluble or emulsifiable in oil to those which are soluble or emulsifiable in water can be prepared. The alkali metal and ammonium salts are readily water-soluble, whereas the free acids and especially the esters become oil-soluble as the number of carbon atoms increases.

Particular examples of water-soluble ammonium salts are the tri-(diethanolammonium) and the tri-(triethanolammonium) salts.

The greatest advantage is that the compounds, as ultraviolet-B filters, are no less than twice as efficient as the most powerful agents known hitherto, ie. in the preparation of sun screen agents no more than half the amount of active ingredient is in general required in order to achieve a sun protection action similar to that of the prior art. The filter action in the ultraviolet-B range can be utilzed in general in cosmetic formulations as well as for stabilizing plastics, dye formulations or surface coatings. The compounds can of course also be employed in combination with other sun screen agents.

A cosmetic preparation or formulation contains in general from 0.1 to 10, preferably from 0.2 to 5, % by weight, based on the formulation, of the compound, as well as carriers or diluents conventionally used in cosmetics, with or without conventional cosmetic auxiliaries.

The cosmetic formulations may also contain the conventional solid, semi-solid or liquid carriers or diluents, or mixtures of these, with or without other conventional cosmetic auxiliaries.

The nature of the carrier, auxiliary or diluent determines whether the finished preparation containing a sun screen agent is, for example, a solution, an oil, a cream, an ointment, a lotion, a gel or a powder. Formulations of this type may be found, for example, in Fette und Seifen, 53 (1951), 694–699, Seifen, Öle, Fette, Wachse (1955), 147, and H. Janistyn, Handbuch der Kosmetika und Riechstoffe, Volume 3 (1973).

Examples of conventional cosmetic auxiliaries which may be used as additives are emulsifiers, eg. fatty alcohol oxyethylates, sorbitan fatty acid esters or lanolin derivatives, thickeners, eg. carboxymethylcellulose or crosslinked polyacrylic acid, preservatives and perfumes. Examples of suitable bases for protective sun oils are vegetable oils, eg. groundnut oil, olive oil, sesame oil, cottonseed oil, coconut oil, grapeseed oil and castor oil, as well as mineral oils, such as paraffin oil and especially liquid paraffin, synthetic fatty acid esters and the glycerides.

Examples of bases for ointments are white petroleum jelly, lanolin, emulsifying aqueous wool fat alcohols (eg. ®Eucerin) and polyethylene glycols.

Examples of bases for creams are glycerol, polysaccharides and tylose, or amongst fats and waxes, cetyl alcohol, lanolin, cocoa butter, beeswax, stearic acid, stearyl alcohol, glycerol monostearate and natural and mineral oils and fats.

Examples of bases for emulsions are mixtures of stearyl glycol, a vegatable and/or mineral oil, such as almond oil, paraffin oil or white petroleum jelly, and water, or mixtures of ethyl alcohol, water, lanolin and tragacanth, or mixtures of ethyl alcohol, stearin, water, tragacanth and glycerol, or mixtures of stearic acid, paraffin oil, propyl or isopropyl alcohol and water.

When used for stabilizing plastics, dyes and other light-sensitive industrial materials, the products used according to the invention are employed in general in an amount from 0.2 to 5% by weight, this being mixed with the particular material.

The examples which follow illustrate the invention without implying any limitation thereof.

EXAMPLE 1

16.2 parts of ethylhexyl p-aminobenzoate and 4.0 parts of cyanuric chloride were dissolved in a gasoline cut boiling in the range from 140° to 170° C., and the solution was then refluxed for from 4 to 8 hours. The resulting reaction mixture was cooled, and the product was then recrystallized from gasoline boiling in the range from 120° to 130° C.

Mp: 128° C.; yield 70% of theory of 1,3,5-tris-(p-(2-ethylhex-1-yloxycarbonyl)-anilino)-s-triazine; ultraviolet (in ethanol): $E_1 \, _{cm}^{1\%} = 1{,}585$ at 313.3 nm, $E_1 \, _{cm}^{1\%} = 456$ at 218.7 nm.

The corresponding n-hexyl and 3,5,5-trimethylpentyl esters were prepared in a similar manner.

The i-amyl ester is obtained from i-amyl p-aminobenzoate in a similar manner. Mp: 177°–180° C.; ultraviolet (in ethanol): $E_1 \, _{cm}^{1\%} = 1{,}854$ at 313.5 nm, $E_1 \, _{cm}^{1\%} = 596$ at 217.7 nm.

The tripotassium salt of s-triazine-1,3,5-tris-(p-aminobenzoic acid) melts at above 250° C. Ultraviolet (in ethanol): $E_1 \, _{cm}^{1\%} = 1{,}213$ at 298.5 nm.

EXAMPLE 2

1,3,5-Tris-(p-ethoxycarbonylanilino)-s-triazine 82.6 g of ethyl p-aminobenzoate and 30.75 g of cyanuric chloride in 1,500 ml of xylene were refluxed for 8 hours, hydrogen chloride escaping during this procedure. Thereafter, 1 liter of xylene was added, and the suspension, at 80°–90° C., was washed neutral with saturated sodium bicarbonate solution and then cooled to room temperature, and the product was filtered off over a glass suction filter. The white crystals obtained were washed with ethanol and dried. Mp: 218°–223° C.; yield: 97% of 1,3,5-tris-(p-ethoxy-carbonylanilino)-s-triazine; ultraviolet (in ethanol): $E_1 \, _{cm}^{1\%} = 2{,}080$ at 313 nm, $E_1 \, _{cm}^{1\%} = 699$ at 218 nm.

EXAMPLE 3

1,3,5-Tris-(p-(oct-1-yloxycarbonyl)-anilino)-s-triazine 75 g of octyl p-aminobenzoate and 18.5 g of cyanuric chloride in 1,000 ml of xylene were heated at 140° C. for 8 hours. After the evolution of hydrogen chloride was complete, the reaction solution was cooled to 90° C., washed twice with saturated sodium bicarbonate solution and once with water and then cooled to room temperature. The white crystals precipitated were filtered off under suction.

Yield: 79% of theory; mp: 140° C., ultraviolet (in ethanol): $E_1 \, _{cm}^{1\%} = 1{,}555$ at 313.3 nm, $E_1 \, _{cm}^{1\%} = 447$ at 218 nm.

EXAMPLE 4

1,3,5-Tris-(p-(3,7-dimethyloct-1-yloxycarbonyl)-anilino)-s-triazine 18.5 g of cyanuric chloride and 84 g of tetrahydrogeranyl p-aminobenzoate in 1,000 ml of xylene were heated at 140° C. for 8 hours. After the evolution of hydrogen chloride was complete, the reaction solution was cooled, washed, at 90° C., twice with saturated sodium bicarbonate solution and once with water, and then cooled to room temperature. The white crystals precipitated were filtered off under suction and dried.

Yield: 50% of theory; mp: 120° C., ultraviolet (in ethanol): $E_{1\ cm}^{1\%}$ 1,416 at 313.3 nm, $E_{1\ cm}^{1\%}=418$ at 218.4 nm.

EXAMPLE 5

1,3,5-Tris-(p-(dec-1-xloxycarbonyl)-anilino)-s-triazine 83 g of decyl p-aminobenzoate and 18.5 g of cyanuric chloride in 1,000 ml of xylene were heated at 140° C. for 8 hours. After the evolution of hydrogen chloride was complete, the reaction solution was cooled to 90° C., washed twice with saturated sodium bicarbonate solution and once with water, and then cooled to room temperature. The white crystals precipitated were filtered off under suction and dried.

Yield: 69% of theory; mp: 140° C.; ultraviolet (in ethanol): $E_{1\ cm}^{1\%}=1,416$ at 313.3 nm, $E_{1\ cm}^{1\%}=418$ at 217.8 nm.

EXAMPLE 6

1,3,5-Tris-(p-(dodec-1-yloxycarbonyl)-anilino)-s-triazine 18.5 g of cyanuric chloride and 92 g of dodecyl p-aminobenzoate in 1,000 ml of xylene were heated at 140° C. until HCl gas was no longer evolved. After 8 hours, the reaction solution was cooled to 80° C., washed twice with saturated sodium bicarbonate solution and once with water, and then cooled to room temperature. The precipitated crystals were filtered off under suction and dried.

Yield: 82% of theory; mp: 139°–140° C.; ultraviolet (in ethanol): $E_{1\ cm}^{1\%}=1,268$ at 313.2 nm; $E_{1\ cm}^{1\%}=384$ at 218.1 nm.

EXAMPLE 7

1,3,5-Tris-(p-(3-oxa-5-hydroxypent-1-yloxycarbonyl)-anilino)-s-triazine 106 g of diethylene glycol and 123 g of triazine-1,3,5-tris-(p-aminobenzoic acid) were dissolved in 1,000 ml of xylene, 3 g of p-toluenesulfonic acid were added, and the mixture was refluxed for 10 hours, during which 18 g of water were separated off. The resulting suspension was filtered through a glass suction filter, and the crystals obtained were dried.

Yield: 89% of theory; mp: >250° C.; ultraviolet (in dimethylsulfoxide): $E_{1\ cm}^{1\%}=1,369$ at 313.5 nm.

EXAMPLE 8

1,3,5-Tris-(p-(3-oxa-5-methoxypent-1-yloxycarbonyl)-anilino)-s-triazine 75 g of methyldiglycol p-aminobenzoate and 18.5 g of cyanuric chloride in 1,000 ml of xylene were heated at 140° C. for 8 hours. After the evolution of hydrogen chloride was complete, the mixture was cooled to room temperature and the precipitated product was filtered off, washed three times with xylene and dried under reduced pressure.

Yield: 90% of theory; mp: 129° C.; ultraviolet (in ethanol): $E_{1\ cm}^{1\%}=1,616$ at 313.5 nm, $E_{1\ cm}^{1\%}=495$ at 217.7 nm.

The Examples which follow illustrate various use forms of the novel sun screen agents.

EXAMPLE 9

A sun screen emulsion has the following composition:

| | | |
|---|---|---|
| (a) | glycerol monostearate | 6.0 parts |
| | Triglyceryl ester of a $C_8/C_{12}$—carboxylic acid | 5.0 parts |
| | Paraffin oil | 5.0 parts |
| | Product as described in Example 1 | 1.5 parts |
| | An adduct of tallow alcohol with 25 moles of ethylene oxide | 1.0 part |
| | An adduct of tallow alcohol with 6 moles of ethylene oxide | 1.0 part |
| | Propylene 1,2-glycol | 3.0 parts |
| | Silicone oil | 0.2 part |
| | Preservatives | 0.5 part |
| | Perfume oil | 0.2 part |
| | Water | 76.6 parts |
| (b) | Glycerol monostearate | 6.0 parts |
| | Paraffin oil | 5.0 parts |
| | Isopropyl myristate | 5.0 parts |
| | Product as described in Example 1 | 1.5 parts |
| | An adduct of tallow alcohol with 25 moles of ethylene oxide | 2.0 parts |
| | An adduct of tallow alcohol with 6 moles of ethylene oxide | 2.0 parts |
| | Silicone oil | 0.3 part |
| | Preservatives | 0.5 part |
| | Perfume oil | 0.2 part |
| | Water | 74.5 parts |

EXAMPLE 10

An oil-in-water sun screen cream has the following composition:

| | |
|---|---|
| Glycerol monostearate | 8.0 parts |
| Cetyl alcohol | 2.0 parts |
| An adduct of tallow alcohol with 25 moles of ethylene oxide | 2.0 parts |
| An adduct of tallow alcohol with 6 moles of ethylene oxide | 2.0 parts |
| Isopropyl myristate | 15.0 parts |
| Product as described in Example 1 | 1.5 parts |
| Paraffin oil | 5.0 parts |
| Propylene 1,2-glycol | 3.0 parts |
| Preservatives | 0.5 part |
| Perfume oil | 0.2 part |
| Water | 60.8 parts |

EXAMPLE 11

A water-in-oil sun screen cream has the following composition:

| | |
|---|---|
| Isopropyl myristate | 20.0 parts |
| Paraffin oil | 5.0 parts |
| Microcrystalline wax | 6.0 parts |
| Sorbitan sesquioleate | 4.0 parts |
| Product as described in Example 1 | 1.5 parts |
| Magnesium stearate | 1.0 part |
| Aluminum stearate | 1.0 part |
| Propylene 1,2-glycol | 3.0 parts |
| Preservatives | 0.5 part |
| Perfume oil | 0.3 part |
| Water | 57.7 parts |

-continued

A sun screen foam has the following composition:
| | | |
|---|---|---|
| Stearin | 3.0 | parts |
| Cetyl alcohol | 1.0 | part |
| Glycerol ester of a $C_8$–$C_{12}$— carboxylic acid | 5.0 | parts |
| Paraffin oil | 5.0 | parts |
| Product as described in Example 1 | 1.5 | parts |
| Adduct of a fatty alcohol with 25 moles of ethylene oxide | 1.0 | part |
| Silicone oil | 0.1 | part |
| Triethanolamine | 0.3 | part |
| Propylene 1,2-glycol | 3.0 | parts |
| Preservatives | 0.5 | part |
| Perfume oil | 0.2 | part |
| Water | 79.4 | parts |

We claim:

1. A compound of the formula I:

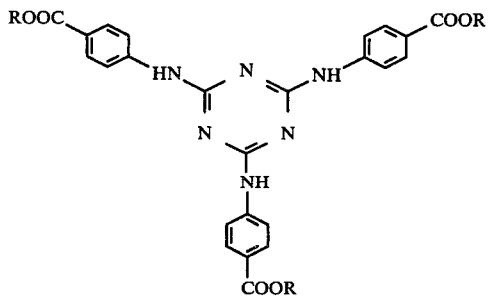

wherein the individual radicals R are identical and are each $C_6$–$C_{12}$ alkyl, or a polyoxyethylene radical which contains 1 to 6 ethylene oxide units and whose terminal OH group is methylated.

2. The compound of claim 1 wherein R is ethylhexyl.

3. The compound of claim 2 wherein R is 2-ethylhexyl.

* * * * *